United States Patent [19]
Yamasaki et al.

[11] Patent Number: 4,965,198
[45] Date of Patent: Oct. 23, 1990

[54] MONOCLONAL ANTIBODY AND METHOD OF MANUFACTURING HYBRIDOMA PRODUCING THE SAME

[75] Inventors: Masahiko Yamasaki; Yoshitaka Nagai, both of Tokyo, Japan

[73] Assignee: Konica Corporation, Tokyo, Japan

[21] Appl. No.: 186,353

[22] Filed: Apr. 26, 1988

Related U.S. Application Data

[63] Continuation-in-part of Ser. No. 942,977, Dec. 22, 1986, abandoned.

[30] Foreign Application Priority Data

| Dec. 24, 1985 | [JP] | Japan | 60-289245 |
| Apr. 27, 1987 | [JP] | Japan | 62-103850 |
| Apr. 28, 1987 | [JP] | Japan | 62-103012 |
| Jul. 1, 1987 | [JP] | Japan | 62-165890 |

[51] Int. Cl.$^5$ ............... C12N 5/00; C12P 21/00
[52] U.S. Cl. ............... 435/70.21; 435/240.27; 935/104; 935/110; 530/387
[58] Field of Search ............... 435/68, 172.2'240.27; 530/387; 935/104, 110

[56] References Cited

PUBLICATIONS

Hashimoto, Y., et al., J. Biochem 91, 1039–1046 (1982).
Higashi, H., et al., Biochem, Biophys. Research Comm. 79, 388–395 (1977).
Fugi, Y., et al., Mol. Immunol. 19, 87–94 (1982).
Male, D. K., et al., Autoimmunity: Experimental Clinical Aspects. Annuals N.Y. Acad. Science vol. 475, 94–105, 1986.
Theofilopoulos, A. N. In: Basic & Clinical Immunology Edited by Stites et al., Lange Medical Publ, of Altos, Calif. pp. 152–186, 1984.
Natoli, et al. Cancer Research 46, 4116–4120, 1986.
Andrezejewski, C., et al. J. Immunol. 126, 226–231.
Livingston, et al. J. Immunol. vol. 135, pp. 1505–1509, 1985.

*Primary Examiner*—Christine Nucker
*Assistant Examiner*—Karen I. Krupen
*Attorney, Agent, or Firm*—Finnegan, Henderson, Farabow, Garrett, and Dunner

[57] ABSTRACT

A monoclonal antibody specific to a sugar chain containing N-glycolylneuraminic acid and has an ability to bind at least to N-glycolyl $GM_2$ ganglioside, and producing methods of a hybridomas which produce the monoclonal antibodies are disclosed. The antibodies are extremely useful for clarification of carcinogenesis mechanism, cancer diagnosis and therapy. The hybridomas are manufactured by using an animal with autoimmune disease.

39 Claims, 5 Drawing Sheets

MONOCLONAL ANTIBODY AND METHOD OF MANUFACTURING HYBRIDOMA PRODUCING THE SAME

CROSS REFERENCE TO RELATED APPLICATION

This application is a continuation-in-part of application Serial No. 942,977, filed Dec. 22, 1986, now abandoned, the entire disclosure of which is relied upon and incorporated by reference herein.

FIELD OF THE INVENTION

This invention relates to a monoclonal antibody specific to a chain containing N-glycolylneuraminic acid and a method for manufacturing a hybridoma which produces the above-mentioned monoclonal antibody.

Also, this invention relates to a method for manufacturing a hybridoma producing a monoclonal antibody which has an ability to bind at least to N-glycolyl $GM_2$ ganglioside and a monoclonal antibody manufactured by the method.

BACKGROUND OF THE INVENTION

Glycolipids are components of a plasma membrane, and various molecular species of glycolipids exist according to the differences of the kinds, number and combining manners of sugar components as well as are distributed specific to species, organs and cells. It has been clarified that glycolipids take an important role related to the growth and differentiation control and to the cellular interaction, and that glycolipids function as receptors of bacteriotoxins, hormones and others and as immunological determinants such as blood group substrates. In addition, some glycolipids have been shown to be tumor antigens due to qualitative and quantitative changes in their composition in association with cell canceration.

Other glycolipids work as regulators of the cell growth mechanism through a growth factor and protein kinase. These instances suggest that the composition change of glycolipids can directly relate to the carcinogenesis mechanism.

On the other hand, establishment of a cell line which produces homogeneous antibodies specific to a single antigenic determinant was reported by Milstein et. al. (*Nature*, 256, 495-497 (1975)), enabling qualitative and quantitative analyses of substances existing in a very small amount. By using this technique to detect tumor antigens, a number of monoclonal antibodies have been prepared, some of which have been proved to recognize sugar chains of glycolipids or glycoproteins (*J. Natl. Cancer Inst.* 71, 231-251, (1983)).

For example, monoclonal antibodies against human melanoma, which react with glycolipids such as $GD_2$ ganglioside or $GD_3$ ganglioside, have been obtained. Monoclonal antibody NS19-9, specific to pancreas cancer, reacts with glycolipids having a sugar chain of sialosyl Lewis A type. These antibodies are useful for cancer diagnosis and observation in prognosis and have been studied for use in therapy. The qualitative and quantitative changes of glycolipids are resulted from changes of glycosyltransferase activity in the sugar chain biosynthesis mechanism due to abnormal DNA manifestation. These changes cause abnormal sugar chain structures which are not present in normal tissues. These sugar structures can be used as tumor markers.

Therefore, the importance and usefulness of glycolipids as tumor antigens and tumor markers have been recognized and expected to be applied in the clinical field such as diagnosis and therapy.

When necessary to discriminate particularly between the kinds of sialic acids in this description hereinafter, such discrimination will be made by attaching the prefix, 'N-glycolyl' or 'N-acetyl', to the name of a glycolipid.

Among glycolipids, ganglioside is a general term for the glycolipids which contain one or more sialic acid in their sugar chains. As a sialic acid, N-acetylneuraminic acid and N-glycolylneuraminic acid are common. Sialic acids are extensively detected in various organs, cells and body fluids of animal species, while N-glycolylneuraminic acid has not been found in normal humans or chickens.

Heterophile antibodies which are found in patients with serum diseases and agglutinate erythrocytes of sheep, horses, pigs, rabbits and guinea pigs are called H-D antibodies. The antigens recognized by the H-D antibodies are called H-D antigens. That some gangliosides which contain N-glycolylneuraminic acid have the H-D antigen activity was reported (*Biochem. Biophys. Res. Commun.* 79. 388-395 (1977)), and a sugar structure, NeuGcα2-3 Gal- was identified a the chief antigen determinant.

Recently, it was reported that an antibody reacting with various gangliosides having the H-D antigen activity was prepared from serum of chickens immunized by N-glycolyl $GM_3$ ganglioside ($II^3$NeuGc-LacCer) having the H-D antigen activity, and that using this antibody N-glycolylneuraminic acid was proved to be present characteristically in human cancer tissues (*Biken J.* 25, 47-50 (1982)). In addition, several kinds of H-D antigen active gangliosides containing N-glycolylneuraminic acid were detected in the glycolipids extracted from human colon cancer tissues, and glycoproteins containing a H-D antigen-active sugar chain were detected in teratoma tissues (*Gann*, 75, 1025-1029 (1984)). The H-d antigen-active glycolipids which were detected in human colon cancer tissues were identified as N-glycolyl $GM_2$ ganglioside, N-glycolyl $GM_3$ ganglioside, O-acyl-N-glycolyl $GM_3$ glanglioside and $IV^3$-NeuGc-nLcOse Cer by using antibodies prepared from chickens, and these glycolipids were not detected in normal tissues (*Cancer Res.* 45, 3796-3802 (1985)). In a cell line of Marek's disease, lymphoma of chickens, gangliosides having the H-D antigen activity were detected (*J. Biochem.* (Tokyo), 95, 785-794 (1984)).

Because N-glycolylneuraminic acid and sugar chains containing N-glycolylneuraminic acid are considered as tumor-associated antigens, it is of great importance for cancer diagnosis to detect these acid and sugar chains with high sensitivity and precision.

In order to detect efficiently N-glycolylneuraminic acid, immunoassays are considered to be superior in view of the sensitivity of detection and the accuracy.

Antibodies reacting with a sugar chain which contains N-glycolylneuraminic acid having the H-D antigen activity have been obtained from serum of chickens immunized by purified glycolipid antigens (Molec. Immunol., 19. 87-94 1982)

Polyclonal antibodies having a high specificity to N-glycolyl $GM_2$ ganglioside can be obtained by immunizing a chicken against N-glycolyl $GM_2$ ganglioside. (Biochemical and Biophysical Research Communications, Vol. 129, pp. 334-341, 1985). Polyclonal antibodies having a reactivity with N-glycolyl $GM_2$ ganglioside and N-glycolyl$GM_3$ ganglioside can be obtained by immunizing a chicken against N-glycolyl $GM_3$ ganglioside. (Cancer Research, Vol. 45 pp. 3796–3802, 1985)

This method, however, has several drawbacks; specifically (1) a large number of purified antigens are required each time the antiserum is needed, (2) the antiserum varies in affinity and titer due to mainly individual differences of immunized animals, (3) for the purification of the desired antibodies, tedious and time-consuming procedures are necessary because of inclusion of undesired antibodies, (4) the shortage of the quantity of the antiserum prepared one time. Thus, in order to carry out an immunoassay with accuracy and the most effectiveness, it has been desired that homogeneous antibodies with stable quality and no inclusion of the other antibodies are able to be supplied in a large quantity. Such manufacturing method of antibodies has been reported as the monoclonal antibody producing technique.

As for monoclonal antibodies specific to sugar chains containing N-glycolyneuraminic acid which have the H-D antigen activity as well as hybridomas having the ability of producing the said antibodies, however, manufacturing have not been reported.

On the other hand, there has been a report that a human monoclonal antibody capable of specifically recognizing melanoma obtained by transforming the lymphocytes of a melanoma patient with EB virus, such human monoclonal antibody reacts with $GM_2$ ganglioside. (Proceedings of the National Academy of Sciences of the U.S.A.. 80, pp. 5392–5396, 1985).

There has also been another report that human erythro-leukemia cells deposit $GM_2$ ganglioside threrein, despite of the fact that almost no $GM_2$ ganglioside is present in normal erythrocytes. (Blood, 62, pp. 1230–1241, 1983).

There has further been a disclosure that, when making use of monoclonal antibody capable of recognizing N-acetyl $GM_2$ ganglioside and N-glycolyl $GM_2$ ganglioside each obtained by immunizing mouse melanoma $GM_2$ ganglioside is manifested mainly in cancerous cells derived from neuroectoderm. (Cancer Research, 46, pp. 4116–4120, 1986).

Accordingly. N-acetyl $GM_2$ ganglioside and N-glycolyl $GM_2$ ganglioside are regarded as tumor associated antigens and it is essential from the viewpoint of cancer diagnoses to detect these gangliosides with high sensitivity and accuracy.

As mentioned above, N-glycolyl $GM_2$ ganglioside, its related glycolipids and sugar chain structures are substantially essential as tumor associated antigens. Therefore. monoclonal antibodies having a reactivity with N-glycolyl $GM_2$ ganglioside, such as those having a reactivity with N-glycolyl $GM_2$ ganglioside and N-acetyl $GM_2$ ganglioside and those having a specific reactivity with N-glycolyl $GM_2$ ganglioside and other glycolipid-containing N-glycolyl neuraminic acid, are very useful for the diagnosis of various diseases and especially for the diagnoses of human cancers by way of the diagnoses of organs and cells, blood and urine, imaging, or the like. These monoclonal antibodies are also applicable to a missile therapy of bonding a drug to an antibody, or to a therapy utilizing a cytotoxicicity, and they are further applicable to the diagnoses of detecting an antibody against a sugar chain. In the fundamental studies of the relation between a sugar chain and a carcinogenesis mechanism, the structures of sugar chains and glycolipids or the in vivo functional roles thereof, and so forth, various monoclonal antibodies having a reactivity with N-glycolyl $GM_2$ ganglioside can be used as a useful means.

In this connection, it may be considered to be essential that a monoclonal antibody capable of recognizing at least N-glycolyl $GM_2$ ganglioside is manufactured.

However, there are the known facts that N-glycolylneuraminic acid is present in the bodies of many kinds of animals including mice but human and chicken, and that N-glycolylneuraminic acid-containing glycolipids including N-glycolyl $GM_2$ ganglioside which is the subject of the invention, are spread into the system of mice. These glycolipids are the autoantigens of their own. The immunogenicity thereof has been considered to be very weak and, therefore, in the conventional methods using normal mice such as Balb/c mouse and so forth as immune animals, it has been very difficult to obtain a monoclonal antibody capable of producing hybridomas against glycolipids containing N-glycolylneuraminic acid, including N-glycolyl $GM_2$ ganglioside.

On the other hand, it has been known that animals having an autoimmune disease produce an antibody against an auto-antigen such as an anti-nuclear antibody, antierythrocyte antibody or the like, as described in Immunological Review, Vol. 55, pp. 121–154, 1981. The present inventors devised a method that animals having an autoimmune disease such as, particularly, mice having autoimmune disease, are sensitized to an immunity and, thereby, an immunity reactivity may be increased against N-glycolylneuraminic acid containing glycolipids which may be considered to be autoantigens, and hybridoma may be produced. The inventors tried the method and then achieved the object thereof.

In the course of trying the method, the inventors found that the hybridoma can readily be prepared so as to produce a monoclonal antibody capable of recognizing, particularly. N-glycolyl $GM_2$ ganglioside, so that this invention can be achieved.

SUMMARY OF THE INVENTION

It is the first object of this invention to provide monoclonal antibodies specific to a sugar chain containing N-glycolylneuraminic acid which have the H-D antigen activity.

The second object of this invention is to provide a manufacturing method for hybridomas which produce the monoclonal antibodies specific to a sugar chain containing N-glycolylneuraminic acid which have the H-D antigen activity.

The third object of this invention is to provide a manufacturing method for hybridomas producing monoclonal antibodies which have an ability to bind at least N-glycolyl $GM_2$ ganglioside and monoclonal antibodies manufactured by the method.

An outline of this invention is that the invention relates to monoclonal antibodies specific to a sugar chain containing N-glycolylneuraminic a id and also to a manufacturing method of hybridomas producing the antibodies. This method features the use of mice with autoimmune disease as immunized subjects.

Another outline of this invention is that the invention relates to a manufacturing method of hybridomas producing monoclonal antibodies which have an ability to bind at least to N-glycolyl $GM_2$ ganglioside and to monoclonal antibodies manufactured by the method.

As used herein the term 'specific to a sugar chain containing N-glycolylneuraminic acid' refers to monoclonal antibodies that do not react with a sugar chain containing N-acetylneuraminic acid or a sugar chain containing no sialic acid.

The inventors tried to manufacture the monoclonal antibodies specific to the H-D antigen active gangliosides containing N-glycolylneuraminic acid, and the hybridomas producing the monoclonal antibodies. Also, the inventors tried to easily manufacture the hybridomas producing the monoclonal antibodies which have an ability to bind at least to N-glycolyl $GM_2$ ganglioside and the monoclonal antibodies. The invention has been completed after a thorough examination.

As prescribed, this invention provides new monoclonal antibodies. These monoclonal antibodies are extremely useful for clarification of carcinogenesis mechanism, cancer diagnosis and therapy.

DETAILED DESCRIPTION OF THE INVENTION

Figure 1:
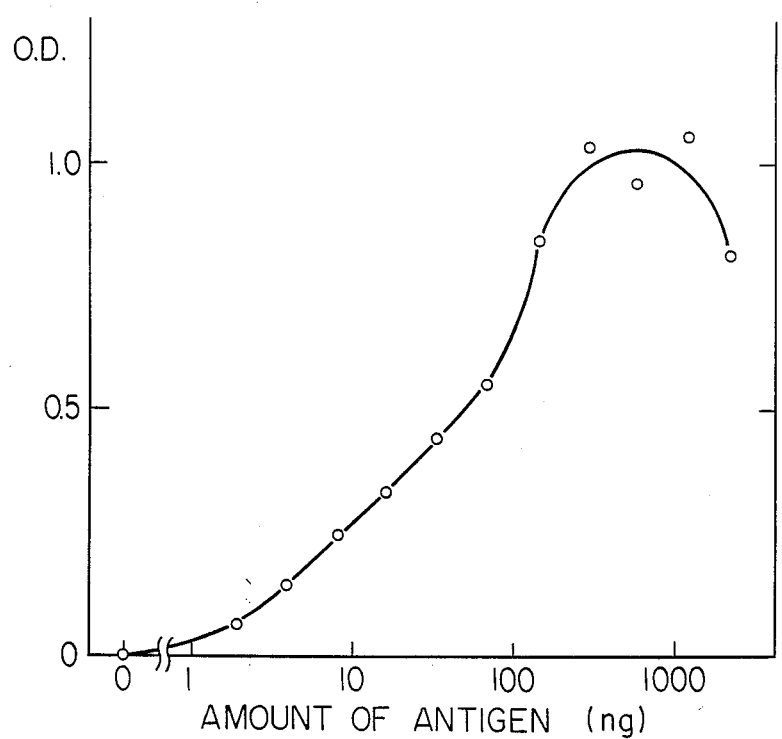
FIG. 1 exhibits the reactivity of the antibody PyK-2 with N-glycolyl $GM_2$ ganglioside by varying the antigen amount in the ELISA.

Structures of glycolipids described in this specification are as follows:

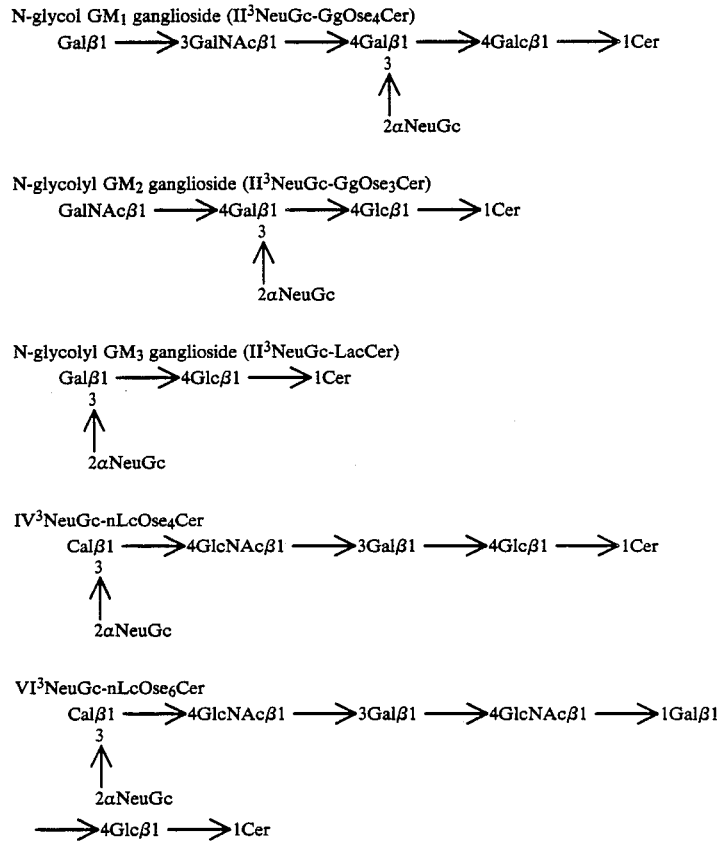

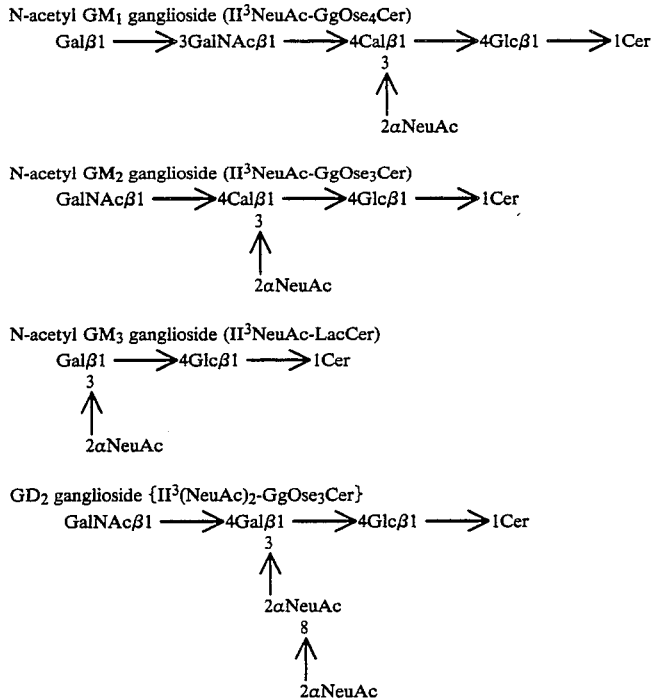

Asialo GM₂ (GgOse₃Cer)

GalNAcβ1→4Galβ1→4Glcβ1→1Cer

CDH (LacCer)

Galβ1→4Glcβ1→1Cer in which Gal represents galactose, Glc represents glucose, GalNAc represents N-acetylgalactosamine, GlcNAc represents N-acetylglucosamine, NeuGc represents N-glycolylneuraminic acid, NeuAc represents N-acetylneuraminic acid and Cer represents ceramide.

The monoclonal antibodies in this invention have the reactivity with one or several kinds of gangliosides having the H-D antigen activity which are considered to be human tumor-associated antigens, and these monoclonal antibodies do not react with gangliosides containing N-acetylneuraminic acid or with glycolipids having no sialic acid.

The sugar chains having the H-D antigen activity which were recognized by the monoclonal antibodies in this invention are present in glycoproteins as well as in glycolipids. Therefore, the monoclonal antibodies in this invention which recognize the sugar chains, possible human tumor-associated antigens, are of great usefulness for cancer diagnosis.

The monoclonal antibodies in this invention are highly useful for human cancer diagnosis by histologic and cytologic examinations, blood and urea analyses, and image diagnosis, and has the possibility to be applied to the missile therapy, i.e. combining drugs to antibodies, as well as the therapy utilizing cytotoxicity.

The antibodies are also useful for detection of the H-D antibody of the monoclonal antibody in this invention.

These monoclonal antibodies can be adopted in the diagnosis and therapy of Marek's disease of chickens.

The monoclonal antibodies can be used in basic studies about the relation between sugar chains and the carcinogenesis mechanism, the roles of sugar chains in living bodies, and others.

The monoclonal antibodies in the invention are obtained in the following procedure.

A preparation containing immunogens is used to immunize animals. Thereupon, the immunized animals are preferred to be selected with consideration of their compatibility with the myeloma used in cell fusion. Mice or rats are preferable. When using glycolipids which contain N-glycolylneuraminic acid, an object of this invention, animals with autoimmune disease are more preferable and mice with autoimmune disease are the most preferable. As the mice with autoimmune disease, there are NZB, NZW, B/WF₁, MRL/1, BXSB male, SL/Ni and other mice available. Normal mice such as Balb/c may be used as immunized animals if the mice become autoimmune by raising their autoantibody producing ability caused by the injection of a polyclonal B cell activator (PBA) such as bacterial lipopolysaccharide (LPS) or dexstran sulfate.

N-Glycolylneuraminic acid is present in many animals including mice.

The glycolipids which contain N-glycolylneuraminic acid including gangliosides with the H-D antigen activity, one of the objects in this invention, are known to exist widely in mouse tissues, so that these glycolipids are autoantigens for mice. Therefore, these glycolipids are thought to have extremely weak immunogenicity. It is very difficult to obtain the monoclonal antibody specific to or against glycolipids containing N-glycolylneuraminic acid according to the conventional methods which use normal mice such as Balb/c mice as immunized animals. On the other hand, it is known that mice with autoimmune disease produce antibodies against autoantigens such as anti-nuclear antibodies or anti-erythrocyte antibodies.

We have completed this invention by trying to manufacture a hybridoma which produces the monoclonal antibodies against the H-D antigen active glycolipids and by finding that the expected hybridoma was manufactured by immunizing mice with autoimmune disease.

By this invention, it is possible to easily manufacture the hybridoma which produces the monoclonal antibody specific to a sugar chain containing N-glycolylneuraminic acid which is considered as autoantigen, or the hybridoma which produce the monoclonal antibody having an ability to bind at least N-glycolyl $GM_2$ ganglioside, and to obtain the said monoclonal antibodies.

As an immunogen, it is possible to use the cell itself that has glycolipids containing N-glycolylneuraminic acid, a ce-11 membrane component separated from the above cell, or glycolipids containing N-glycolylneuraminic acid which are separated from the above cell. It is also possible to use glycolipids in the form of liposome by combining them with phospholipids and cholesterol. Immunization is carried out in a conventional method. One of the above described immunogen is diluted with phosphate-buffered saline (abbreviated as PBS, hereafter) or others and injected intraperitoneally (i.p.) or introvenously (i.v.). At this time, the immunogen may be bound to a carrier such as bovine serum albumin (BSA) or a fungus body, or be injected in conjunction with adjuvant such as Freund's adjuvant or fungus body adjuvant.

In the method of the invention for manufacturing a hybridoma which produces a monoclonal antibody having an ability to bind at least to N-glycolyl $GM_2$ ganglioside, using mice having an autoimmune disease, it is not necessary to use an immunogen.

Judging from the facts that N-glycolyl $GM_2$ ganglioside is present in the erythrocytes of mice, according to Journal of Biochemistry. Tokyo, Vol. 91, pp. 1039–1046, 1982, and that mice having an autoimmune disease produce autoantibodies such as anti-erythrocyte antibodies, it may be considered that mice having an autoimmune disease are in such a state where antibodies against N-glycolyl $GM_2$ ganglioside are produced to serve as anti-erythrocyte autoantibodies or other autoimmune antibodies, or in such a state where these antibodies are apt to be produced. In the case of using such a mouse having an autoimmune disease, therefore, monoclonal antibody-producing hybridomas capable of reacting with N-glycolyl $GM_2$ ganglioside may be prepared without using any immunogen. In the case of using no immunogen, it is not necessary to give any injection to mice having an autoimmune disease, but it is preferable to give the mice an injection of various kinds of adjuvants such as a complete Freund's adjuvant, incomplete Freund's adjuvant, pertussis adjuvant. salmonella adjuvant and so forth so as to increase the immune response of the mice.

The spleen cells removed from the immunized animals are fused with mouse myeloma cells. Various kinds of myeloma cells already known are used such as NS-1, SP-2, X63.6.5.3, P3-U1 and others. Cell fusion is carried out according to known methods in the presence of a fusogen, polyethylene glycol (PEG), or Sendai virus. The preferable ratio of the spleen cell amount to the myeloma cell amount is 1/1 to 10/1, the same as that in a conventional method.

After the fusion, hybridomas are selected by culturing in the conventional selective medium. The above described myeloma cell is not able to survive in HAT medium (medium containing hypoxanthine, aminopterin and thymidine), so that only cells surviving in the HAT medium can be selected.

When colonies of the hybridomas grow sufficiently, screening and cloning are performed.

Screening of the said antibody-producing hybridoma is carried out according to a conventional method such as the ELISA (*Meth. Enzymol.* 70, 419–439 (1980)), the agglutination method, or the double immunodiffusion method.

In a typical procedure, microtiter plates coated with purified-glycolipid antigens are blocked with BSA, incubated with the hybridoma supernatant to be tested, treated with a enzyme-conjugated antibody prepared against a mouse antibody. The presence of the antibody which is combined with the said antigen is confirmed by determining the enzyme activity, and the desired antibody-producing hybridoma is selected.

Cloning is performed by limiting dilution. Hybridomas are distributed on a 96-well microtiter plate in such a way that one or less hybridoma is present in a well, which permits a single colony to grow. In this cloning, it is preferable that mouse thymocytes are added as feeder cells.

By repeating the above cloning, monoclonal hybridomas are obtained.

In order to obtain the monoclonal antibodies in this invention, the hybridomas may be cultured in a suitable medium followed by removing the antibodies from the culture supernatant, or the hybridomas may be injected into mouse intraperitoneally followed by recovering the resulted monoclonal antibodies from the ascites fluid. In addition, it is possible to purify the antibodies by conventional procedures, such as ammonium sulfate precipitation, gel chromatography or ion-exchange column chromatography.

EXAMPLES

The following examples illustrate specific embodiments of the various aspects of the invention. These examples are not intended to limit the invention in any manner.

EXAMPLE 1

(1) Isolation and Purification of Antigen and Various Glycolipids

1. A membrane fraction of rabbit thymus tissue

The rabbit thymus tissue obtained from two rabbits of 6 weeks after birth were homogenized in PBS, and centrifuged at 10,000 g for 1 hour, and the obtained pellet was dispersed in 10 ml of PBS to be used as an immunogen.

2. Glycolipids

Bovine kidneys were homogenized in cold acetone, and a large quantity of cold acetone was added to the solution. The obtained precipitate was extracted subsequently with various mixtures of chloroform, methanol and water (10:20:1, 10:10:0, 20:10:1 in volume). The resulted crude glycolipids were applied to DEAE-Sephadex A-25 column chromatography, and separated into acidic fractions and neutral fractions. The acidic fractions were applied to Iatrobeads (Iatron Laboratories, Inc., Tokyo, Japan) column chromatography, to obtain N-glycolyl $GM_2$ ganglioside. In the same manner, N-glycolyl $GM_3$ ganglioside was obtained from equine erythrocytes, $IV^3$NeuGc-nLcOse$_4$Cer and $VI^3$-NeuGc-nLcOse$_6$Cer from bovine erythrocytes, N-acetyl $GM_2$ ganglioside and N-acetyl $GM_3$ ganglioside from human brains, CDH from human erythrocytes.

N-Acetyl GM$_2$ ganglioside was treated in 1 N formic acid at 100° C for 1 hour, passed through DEAE-Sephadex A-25 column chromatography and Iatrobeads column chromatography, to obtain Asialo GM$_2$. Acidic glycolipid fractions obtained from C3H/He mouse erythrocytes, without purifications, were used for enzyme immunostaining on TLC.

Glycolipid-containing liposome for immunization was prepared in such a way that glycolipid 1 mg, phosphatidylcholine 4 mg, and cholesterol 10 mg were mixed with a chloroform and methanol mixture (1:1 in volume) in a flask, the solvent was thoroughly removed under reduced pressure, and the remained solute was ultra-sonicated in the presence of 5 ml of PBS.

(2) Immunization and Cell Fusion Protocol

1. First time

A membrane fraction of rabbit thymus tissue in PBS solution was emulsified in the same volume of Freund's complete adjuvant, followed by i.p. injection of 400 μl of the mixture into NZB mice (female, 6 weeks old). After 2 weeks, the same process was repeated, except using Freund's incomplete adjuvant this time. After 13 weeks, 100 μl of liposome containing IV$^3$NeuGc-nLcOse$_4$Cer in PBS solution was injected into each mouse i.p. followed by the same process of liposome injection after 2 weeks.

Three days after the last immunization, spleen of the mouse was removed, separated into individual cells, and washed with RPMI 1640 medium. On the other hand mouse myeloma cells X63.6.5.3 at logarithmic growth phase were collected, and washed with RPMI 1640 medium. The $7\times10^7$ spleen cells in a suspension and the $1.4\times10^7$ mouse myeloma cells in a suspension were mixed, and isolated by centrifugation. To the combined cells which were placed on a water bath preheated to 37° C, 1 ml of 50% polyethylene glycol-RPMI 1640 was gradually added for 1 min., and cell fusion was performed by stirring gently for 1 min. Two mililiters of RPMI 1640 medium was added with gentle stirring for 2 min. followed by 7 ml for 2 min. Isolated from the medium by centrifugation, the cells were dispersed with 20 ml of RPMI 1640 medium containing 10% fetus calf serum, and seeded into the wells of two 96-well plates at 0.1 ml/well. The next day, 0.1 ml of HAT medium (RPMI 1640 medium containing $4\times10^{-7}$ M aminopterin, $1.6\times10^5$ M thymidine, $1\times10^4$ M hypoxanthine and 10% fetal calf serum) was added to each well. Every 3 to 4 days thereafter, approximately half of the HAT medium was removed and replaced with fresh HAT medium. After 3 weeks, hybridomas were observed to grow in 80% of the wells.

2. Second Time

A membrane fraction of rabbit thymus tissue in PBS solution was emulsified in the same volume of Freund's complete adjuvant, followed by i.p. injection of 300 μl of the mixture into NZD mice (female, 6 weeks old). Thereafter, 200 μl of PBS solution containing N-glycolyl GM$_3$ganglioside 20 μg which was adsorbed by Salmonella Minnesota bacteria 80 μg pretreated with acid was administered i.v. 5 times at 2-week intervals.

Three days after the last immunization, spleens of the mice were removed, separated into individual cells, and washed with RPMI 1640 medium. On the other hand, mouse myeloma cells X63.6.5.3 at logarithmic growth phase were collected, and washed with RPMI 1640 medium. The $4.7\times10^8$ spleen cells in a suspension and the $9.2\times10$hu 7 mouse myeloma cells in a suspension were mixed, and isolated by centrifugation. To the combined cells which were placed on a water bath preheated to 37° C, 2 ml of 50% polyethylene glycol-RPMI 1640 medium was gradually added for 1 min., and cell fusion was performed by stirring gently for 1 min. Four mililiters of RPMI 1640 medium were added with gentle stirring for 2 min. followed by 14 ml for 2 min. Isolated from the medium by centrifugation, the cells were dispersed with 120 ml of RPMI 1640 medium containing 10% fetal calf serum and seeded into the wells of two 96-well plates at 0.1 ml per well. The next day, 0.1 ml of HAT medium (RPMI 1640 medium containing $4\times10^{-7}$ M aminopterin, $1.6\times10^{-5}$ M thymidine, $1\times10^{-4}$ M hypoxanthine and 10% fetal calf serum) was added to each well. Every 3 to 4 days thereafter, approximately half of the HAT medium was removed and replaced with fresh HAT medium. After 3 weeks, hybridomas were observed to grow in 90% of the wells.

3. Third Time

Immunization was performed in the same way as in the second time except for eight i.v. injections this time.

Cell fusion was done in the same was as in the second time except that $3.6\times10^8$ spleen cells and $7.1\times10^7$ mouse myeloma cells were mixed, and that the fused cells were dispersed with 100 ml of RPMI 1640 medium containing 10% fetal calf serum and seeded into the wells of ten 96-well plates.

After 3 weeks, hybridomas were observed to grow in 80% of the wells.

(3) Hybridoma Subcloning

The antibodies in the culture supernatant of hybridomas were detected by the ELISA.

As antigens, N-glycolyl GM$_2$ ganglioside, N-glycolyl GM$_3$ ganglioside and IV$^3$NeuGc-nLcOse$_4$Cer were used. Antigens of 500 ng were adsorbed with microtiter plates for the ELISA, blocked with 1% BSA in PBS solution, and treated with the culture supernatant. The wells were then treated with peroxidase-conjugated goat antimouse Ig, and the expected antibodies were detected by the determination of the optical density at 492 nm using o-phenylene diamine. Resultingly, among the hybridomas manufactured in the first immunization and cell fusion, an activity was detected in one well and this was named PyK-2, while among the hybridomas manufactured in the second immunization and cell fusion, the activity were detected in two wells and these were named YHD-02and YHD-03, respectively.

Further, among the hybridomas manufactured in the third immunization and cell fusion, the activity were detected in four wells and these were named YHD-04, YHD-05, YHD-06 and YHD-07, respectively.

The above-mentioned hybridomas were transferred from HAT medium to HT medium lacking aminopterin and retransferred to RPMI 1640 medium containing 10% fetal calf serum (FCS) for culture.

The incubated hybridomas were cloned by limiting dilution. Hybridoma cells were diluted, cultured on 96 well plates at 0.8 cells/well together with $4\times10^5$ mouse thymocytes/well, and after 2 weeks, screened for antibody production using the ELISA. Cloning was repeated to obtain stable hybridomas, PyK-2, YHD-02, YHD-03, YHD-04, YHD-05, YHD-06 and YHD-07.

Monoclonal antibodies PyK-1, YHD-02, YHD-03, YHD-04, YHD-05, YHD-06 and YHD-07 were found to be an IgM, IgG$_3$. IgG$_{2a}$, IgM, IgM, IgM and IgM, respectively, by double immunodiffusion and the ELISA.

Hybridomas PyK-2, YHD-02, YHD-03, YHD-04, YHD-05 and YHD-07 were deposited with European Collection of Animal Cells, and the following Provisional Accession Numbers were given thereto, respectively; 86122001, 86122002, 87042208, 86122003, 86122004 and 86122005. The accession number of YHD-07 is described as 86122200 in RECEIPT IN THE CASE OF AN ORIGINAL DEPOSIT and 86122005 in VIABILITY STATEMENT. We think the former may be an erratum. Hybridoma YHD-06 was deposited with Fermentation Research Institute, and the following Provisional Accession Number was give thereto; BP-1839.

EXAMPLE 2

(1) Determination of Antigen-Specificity of PyK-2 using the ELISA.

1. N-Glycolyl $GM_2$ ganglioside, which was used as an antigen and varied stepwise in amount, was adsorbed on plates for the ELISA, and treated with the fourfold-diluted culture supernatant of the hybridomas. After washed with PBS, the plates were treated with peroxidase-conjugated goat anti-mouse immunoglobulin, washed, and the optical density at 492 nm was determined using o-phehylene diamine as a substrate for the reactivity of the antibody. The results are shown in FIG. 1, in which the ordinate represents the optical density at 492 nm and the abscissa the antigen quantity (ng).

2. Using various glycolipids as antigens, 500 ng of each glycolipid was adsorbed on plates for the ELISA. Adding the hybridoma culture supernatant which was diluted stepwise, the reactivity of each antigen with PyK-2 in this invention was studies in the same manner as 1. The results are plotted in FIG. 2, in which the ordinate represents the optical density and the abscissa represents the degree of dilution ($2^{-n}$). Each mark represents the followings, respectively:

white circle (O):N-glycolyl $GM_2$ ganglioside ($II^3$-NeuGc-GgOse$_3$Cer)
black circle (●):N-glycolylGMhd 3 ganglioside ($II\#$NeuGc-LacCer)
white triangle (△):$IV^3$NouGc-nLcOse$_4$Cer
black triangle (▲):$VI^3$NeuGc-nLcOse$_6$Cer
white square (□):N-acetyl $GM_2$ ganglioside ($II^3$-NeuAc-GgOse$_3$Cer) Asialo $GM_2$ (GgOse$_3$Cer)

Figure 2:
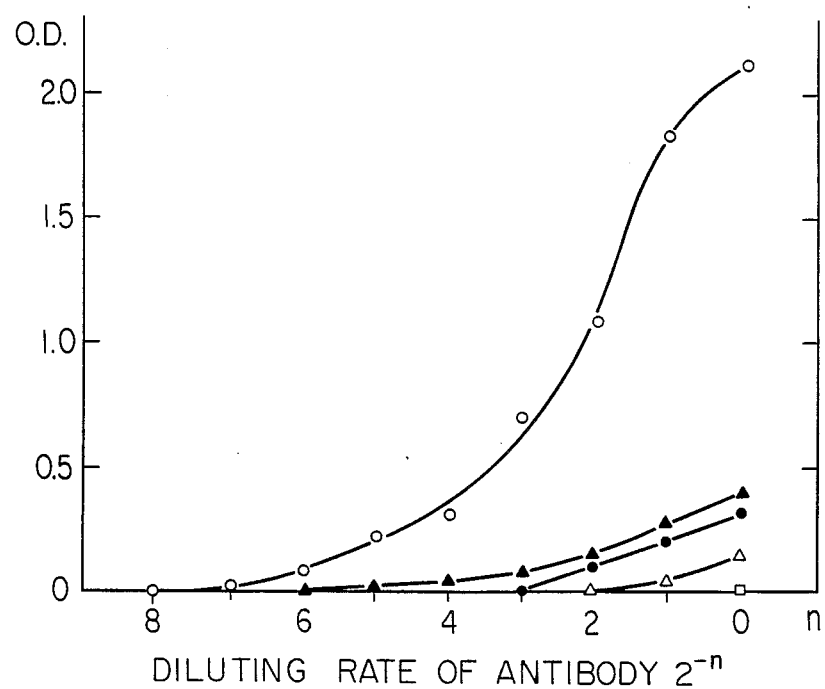
FIG. 2 exhibits the reactivity of the antibody PyK-2 with various glycolipids by varying the antibody amount in the ELISA.

As exhibited in FIG. 2, PyK-2 in the invention was confirmed to have strong reactivity with N-glycolyl $GM_2$ ganglioside and extremely weak reactivity with glycolipids having the structure of N-glycolyl $GM_2$ ganglioside without N-acetylgalactosamine at its end, such as N-glycolyl GMhd 3 ganglioside. Adding to that, PyK-2 was confirmed not to react with N-acetyl $GM_2$ ganglioside and asialo $GM_2$.

(2) Determination of Reactivity of PyK-2 on TLC (Thin Layer Chromatography) Plate Various glycolipids were spotted at 1 cm from the bottom end of TLC plates in the width of 6 mm, and developed with appropriate solvent system. One plate out of 2 received the same procedure, was treated with orcinol reagent to develop color. The other plate underwent the enzyme staining, that is, the various glycolipids were reacted with the antibody PyK-2 in the invention, and treated with peroxidase-conjugated goat antimouse immunoglobulin to detect a blue and purple spot by using 4-chloro-1-naphtol as a substrate.

Figure 3:
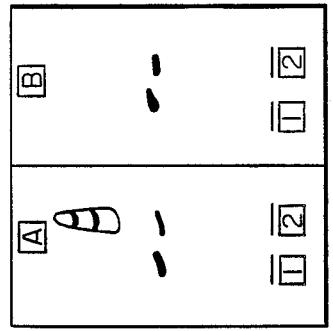
FIG. 3 and FIG. 4 are the spottings of the reactivity of N-glycolyl $GM_2$ ganglioside, N-acetyl $GM_2$ ganglioside, and the crude glycolipid fractions of mouse erythrocytes, which were developed on plates, with the antibody PyK-2 by the enzyme immunostaining.

FIG. 3 is the results of the experiment using N-glycolyl GM ganglioside or N-acetyl $GM_2$ ganglioside as the antigen. The developing solvent was a mixture of chloroform, methanol and 2.5N aqueous ammonia (55:45:10 in volume). A shows the plate of coloration by orcinol reagent, while B shows that of enzyme immunostaining. Number one is the development of N-acetyl $GM_2$ ganglioside and No. 2 is that of N-glycolyl $GM_2$ ganglioside. Apparently, the antibody PyK-2 in the invention is proved to react with N-glycolyl $GM_2$ ganglioside but not to react with N-acetyl $GM_2$ ganglioside.

Figure 4:
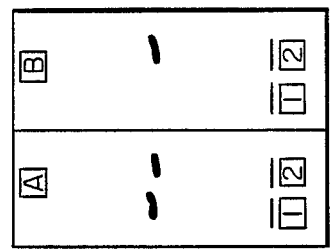

FIG. 4 is the results of the experiment using N-glycolyl $GM_2$ ganglioside or crude acidic glycolipid fractions of mouse erythrocytes as an antigen.

The developing solvent was a mixture of chloroform, methanol and 0.2% calcium chloride solution (55:45:10 in volume). A and B plates are the same as FIG. 3. Number 1 is the development of N-glycolyl $GM_2$ ganglioside, while No. 2 is that of crude acidic glycolipid fractions of mouse erythrocytes. Because C3H/He mouse erythrocytes reportedly contain N-acetyl $GM_4$ ganglioside and N-glycolyl $GM_2$ ganglioside in large amounts as gangliosides (J. Biochem. (Tokyo), 94, 327-330 (1983)), enzyme immunostaining resulted in a color spot at the same Rf value as N-glycolyl $GM_2$ in No. 2.

After the reactivity of the antibody PyK-2 in the invention was examined using extracts from 2 different tissues, bovine kidneys and mouse erythrocytes, PyK-2 was confirmed to react with N-glycolyl $GM_2$ ganglioside itself.

(3) Determination of Antigen-Specificity of PyK-2, YHD-02, YHD-03, YHD-04, YHD-05, YHD-06 and YHD-07 by the ELISA The ELISA was carried out using 0.2 nmol of each glycolipid. The adsorbed antigen on a plate was treated with the hybridoma culture supernatant, and with peroxidase-labelled goat anti-mouse immunoglobulin. The optical density at 492 nm was determined using o-phenylenediamine as a substrate to examine the reactivity of the monoclonal antibodies PyK-I, YHD-02, YHD-03, YHD-04, YHD-05, YHD-06 and YHD-07 with each antigen. The results are indicated in Table-1.

Among the obtained monoclonal antibodies, PyK-2, YHD-04 and YHD-07 showed strong reactivity to N-glycolyl $GM_2$ ganglioside, while YHD-02, YHD-03 and YHD-05 showed reactivity to N-glycolyl GMhd 3 ganglioside and $IV^{3NeucnLcOse}$$_4$Cer as well as to N-glycolyl $GM_2$ ganglioside. YHD-03 did not react with $VI^3$NeuGc-nLcCse$_6$Cer while YHD-02 and YHD-05 reacted therewith. YHD-06 reacted with N-acetyl $GM_2$ ganglioside as well as with N-glycolyl $GM_2$ ganglioside. In other words, PyK-2, YHD-04, YHD-06 and YHD-07 did not show any reactivity to $IV^3$NeuGc-nLcOse$_4$Cer or N-glycolyl GMhd 3 ganglioside, but they showed strong reactivity to N-glycolyl $GM_2$ ganglioside.

TABLE 1

| Glycolipid | PyK-2 | YHD-02 | YHD-03 | YHD-04 | YHD-05 | YHD-06 | YHD-07 |
|---|---|---|---|---|---|---|---|
| N—glycolylGM$_2$-ganglioside | +++ | ++ | ++ | +++ | +++ | +++ | +++ |
| N—glycolylGM$_3$-ganglioside | ± | +++ | +++ | − | ++ | − | − |
| IV$^3$NeuGc-nLcOse$_4$Cer | − | ++ | + | − | ++ | − | − |
| VI$^3$NeuGc-nLcOse$_6$Cer | ± | ++ | − | − | ++ | − | − |
| N—acetylGM$_2$-ganglioside | − | − | − | − | − | +++ | − |
| N-acetylGM$_3$-ganglioside | − | − | − | − | − | − | − |
| AsialoGM$_2$ | − | − | − | − | − | − | − |
| CDH | − | − | − | − | − | − | − |

+++ = Strongly reacted
++ = Reacted
+ = Weakly reacted
± = Scarcely reacted
− = Not reacted

(4) Determination of Antigen-Specificity of YHD-06 in ELISA Method

Various kinds of glycolipids were used as antigens. The antigens varied stepwise in amount were absorbed on the plates for ELISA use and reacted with the culture supernatant of the hybridomas. After washed with PBS, a peroxidase-labelled goat antimouse immunoglobulin antibodies were reacted therewith. After washed with PBS, the absorbance at 492 nm was determined using o-phenylenediamine as a substrate so as to check up the reactivity of the antibodies. The results thereof are shown in FIG. 5, in which the ordinate represents the absorbance at 492 nm and the abscissa the quantities of antigens, respectively, and the marks represent the following.

| White circle: | N-glycolyl GM$_2$ ganglioside (II$^3$ NeuGc-GgOse$_3$ Cer) |
|---|---|
| White triangle: | N-acetyl GM$_2$ ganglioside (II$^3$ NeuAc-GgOse$_3$ Cer) |
| White square: | N-acetyl GM$_1$ ganglioside (II$^3$ NeuAc-GgOse$_4$ Cer) N-glycolyl GM$_1$ ganglioside (II$^3$ NeuGc-GgOse$_4$ Cer) N-acetyl GM$_3$ ganglioside (II$^3$ NeuAc-Lac Cer) N-glycolyl GM$_3$ ganglioside (II$^3$ NeuGc-Lac Cer) GD$_2$ ganglioside (II$^3$ (NeuAc)$_2$-GgOse$_3$ Cer) Asialo GM$_2$ (GgOse$_3$ Cer) CDH (Lac Cer) |

Figure 5:
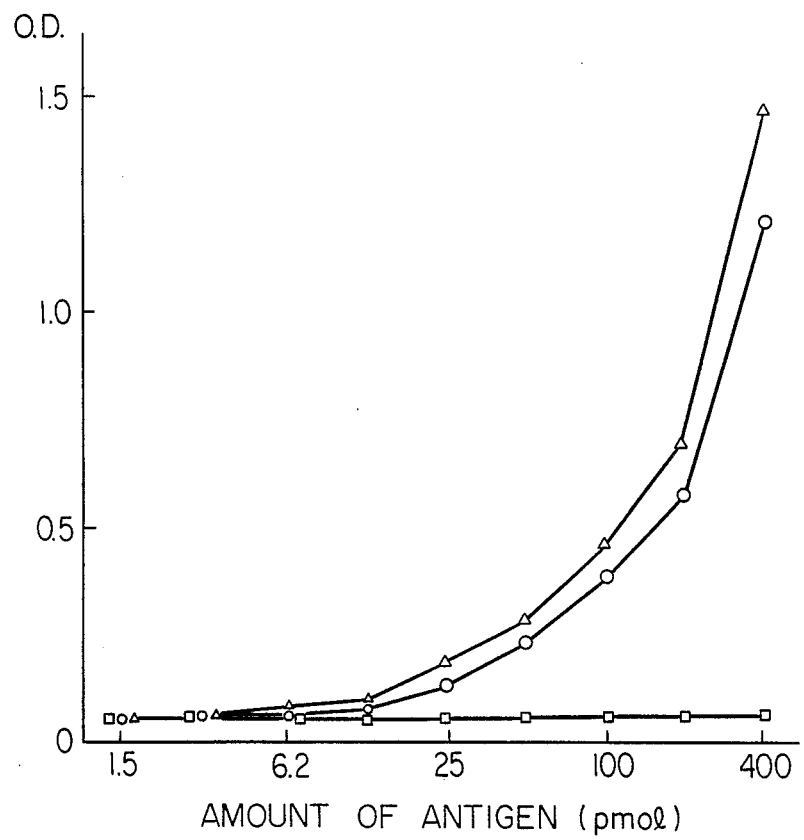
FIG. 5 exhibits the reactivity of the antibody YHD-06 with N-glycolyl $CM_2$ ganglioside, N-acetyl $GM_2$ ganglioside, N-acetyl $GM_1$ ganglioside, N-glycolyl $GM_1$ ganglioside, N-acetyl $GM_3$ ganglioside, N-glycolyl $GM_3$ ganglioside, $GD_2$ ganglioside, asialo $GM_2$ and CDH by varying the antigen amount in the ELISA.

As is obvious from FIG. 5, YHD-06, the antibody of the invention, was confirmed to have a strong reactivity with N-glycolyl GM$_2$ ganglioside and N-acetyl GM$_2$ ganglioside, but not to have a reactivity with other gangliosides and asialo glycolipids.

Figure 7:
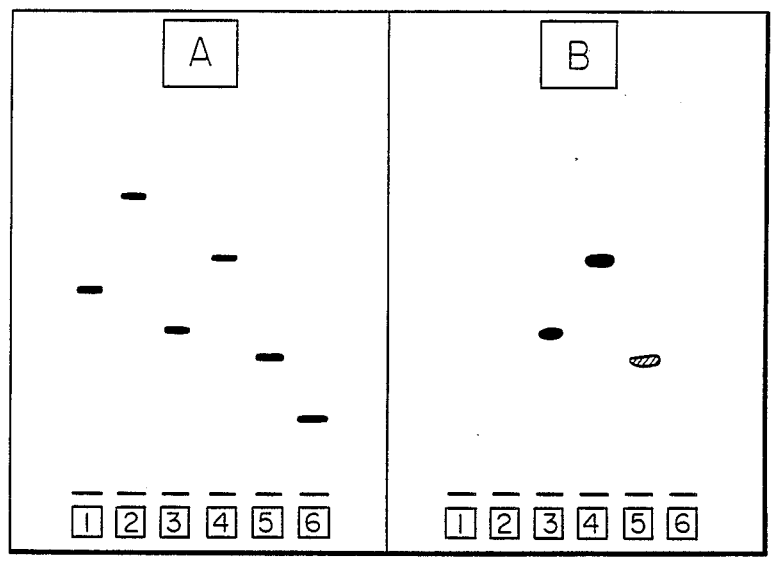
FIG. 7 are the spottings of the reactivity of N-acetyl $GM_2$ ganglioside, N-acetyl GMhd 3 ganglioside, N-glycolyl $GM_2$ ganglioside, N-glycolyl GMhd 3 ganglioside. $IV^3NeuGc$-$nLcOse_4Cer$ and $VI^3NeuGc$-$nLcOse_6Cer$, which were developed on plates, with the antibody YHD-03 by the enzyme immunostaining.

FIG. 7 shows the results of the experiments using six kinds of gangliosides serving as antigens. The developing solvent used was a mixture of chloroform, methanol and 2.5N aqueous ammonia in a volumetric ratio of 55:45:10. A shows the plate colored with orcinol reagent and B shows the plate enzyme-immunostained with YHD-03. Number 1 was developed with N-acetyl GM$_2$ ganglioside, No. 2 was done with N-acetyl GM$_3$ ganglioside, No. 3 was done with N-glycolyl GM$_2$ ganglioside, No 4 was done with N-glycolyl GMhd 3 ganglioside, No. 5 was done with IV$^3$NeuGc-nLcOse$_4$Cer and No.6 was done with VI$^3$NeuGc-nLcOse$_6$Cer respectively.

The monoclonal antibody of the invention, YHD-03, was confirmed to react with N-glycolyl GM$_2$ ganglioside, N-glycolyl GMhd 3 ganglioside and IV$^3$NeuGc-nLcOse$_4$Cer but not to react with VI$^3$NeuGc-nLcOse$_6$Cer and N-acetylneuraminic acid-containing glycolipid.

(5) Determination of Reactivity of YHD-02, YHD-04, YHD-05 and YHD-07 on TLC (Thin Layer Chromatography) Plate Various glycolipids were spotted at 1 cm from the bottom end of TLC plates in the width of 6 mm, and developed with appropriate solvent system. One plate out of two received the same procedure, was treated with orcinol reagent to develop color. The other plate underwent the enzyme staining, that is, the various glycolipids were reacted with the antibodies YHD-02, YHD-04, YHD-05 and YHD-07 in the invention, and treated with peroxidase-conjugated goat anti-mouse immunoglobulin to detect a blue and purple spot by using 4-chloro-1-naphtol as a substrate.

Figure 6:
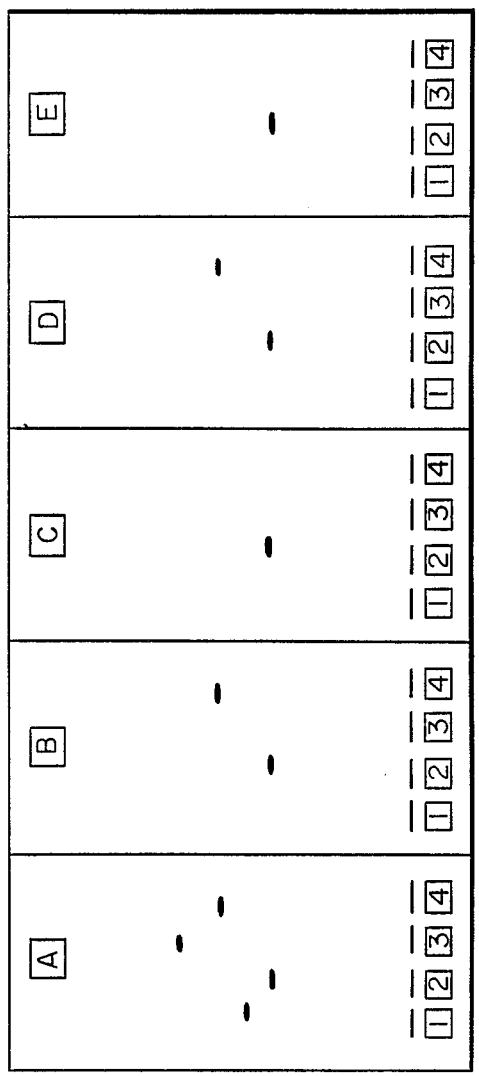
FIG. 6 are the spottings of the reactivity of N-glycolyl $CM_2$ ganglioside, N-acetyl $GM_2$ ganglioside, N-glycolyl GMhd 3 ganglioside, and N-acetyl GMhd 3 ganglioside which were developed on the plates, with the antibody VHD-02, YHD-04, YHD-05 or YHD-07 by the enzyme immunostaining.

FIG. 6 is the results of the experiments using 4 gangliosides as the antigens The developing solvent was a mixture of chloroform, methanol and 2.5 M aqueous ammonia (55:45:10 in volume). A shows the plate of coloration by orcinol reagent, while B to E show that of enzyme immunostaining with YHD-02, YHD-04, YHD-05 and YHD-07, respectively. Number 1 is the development of N-acetyl GM$_2$ ganglioside, No. 2 is that of N-glycolyl GM$_2$ ganglioside, No. 3 is that of N-acetyl GMhd 3 ganglioside, and No. 4 is the development of N-glycolyl GM$_3$ ganglioside. The monoclonal antibodies YHD-02 and YHD-05 in the invention were confirmed to react with N-glycolyl GMhd 3 ganglioside and N-glycolyl GM$_2$ ganglioside, and YHD-04 and YHD-7 were to react with N-glycolyl GM$_2$ ganglioside. Any antibody in this invention was confirmed not to react with glycolipids containing N-acetyl neuramic acid.

(6) Determination of Reactivity of YHD-03 on TLC (Thin Layer Chromatography) Plate Various glycolipids were spotted in a width of 6 mm at 1 cm from the bottom end of TLC plate, and developed with an appropriate solvent system. Out of two plates treated in the same procedure, one plate was treated with an orcinol reagent to develop color. The other plate was treated for an enzyme immunostaining. That is, the above-mentioned various glycolipids were reacted with the antibodies of the invention and further reacted with peroxidase-labelled goat anti-mouse immunoglobulin antibodies. Bluish purple spots were detected by using 4-chloro-1-naphthol as a substrate.

(7) Determination of Reactivity of YHD-06 on a TLC

Various glycolipids were spotted in a width of 6 mm at 1 cm from the bottom end of TLC plates, and were then developed with an appropriate solvent system. Out of the two plates treated in the same manner, one plate was then treated with an orcinol reagent to develop color, and the other plate was enzyme-immunostained. That is, the above-mentioned various glycolipids were reacted with the antibodies of the invention and further reacted with peroxidase-labelled goat antimouse immunoglobulin antibodies. Bluish purple spots were detected by using 4-chloro-1-naphthol as a substrate.

Figure 8:
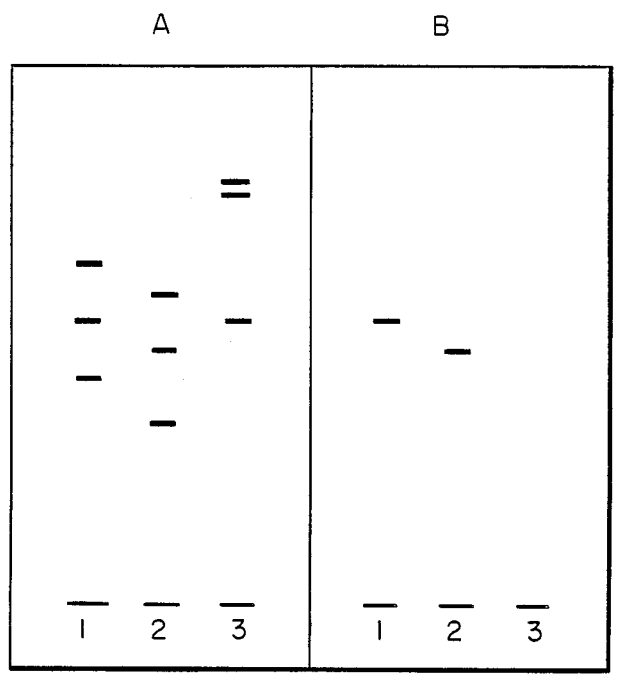
FIG. 8 are the spottings of the reactivity of N-acetyl GMhd 3 ganglioside, N-acetyl $GM_2$ ganglioside, N-acetyl $GM_1$ ganglioside, N-glycolyl GMhd 3 ganglioside, N-glycolyl $GM_2$ ganglioside, N-glycolyl $GM_1$ ganglioside, asialo $GM_2$ and CDH, which were developed on the plates, with the antibody YHD-06 by the enzyme immunostaining.

FIG. 8 shows the results of the experiments using various kinds of glycolipids serving as antigens. The developing solvent used was a mixture of chloroform, methanol and 2.5N aqueous ammonia in a volumetric ratio of 55:45:10. A shows the plate colored with an orcinol reagent and B shows the plate enzyme-immunostained. Number 1 was developed with N-acetyl $GM_3$, ganglioside N-acetyl $GM_2$ ganglioside and N-acetyl $GM_1$ ganglioside. No. 2 was done with N-glycolyl GMhd 3 ganglioside, N-glycolyl $GM_2$ ganglioside and N-glycolyl $GM_1$ ganglioside, and No. 3 was done with asialo $GM_2$ and CDH. respectively. The antibodies of the invention were apparently confirmed to react only with N-glycolyl $GM_2$ ganglioside and N-acetyl $GM_2$ ganglioside.

EXAMPLE 3

Studies on Glycolipids of Rabbit Thymic Tissue on TCL Plate

There has been a report that rabbit thymic tissues, which were used as the immunogens in Example 1, contain many N-glycolylneuraminic acid-containing glycolipids such as N-glycolyl GMhd 3 ganglioside, $IV^3$NeuGc-nLcOse$_4$Cer and so forth (Refer to Biochim, Biophys. Acta, Vol. 665, pp. 205114 213, 1981). However, the presence of N-glycolyl $GM_2$ ganglioside is still unknown. The confirmation thereof was, therefore, tried by making use of monoclonal antibodies.

From the rabbit thymic tissues, crude glycolipids were extracted in order with each of mixed solutions of chloroform. methanol and water in the volumetric ratios of 10:20:1, 10:10:0 and 20:10:1, respectively. The obtained crude glycolipids were applied to DEAE-Sephadex A-25 column chromatography, and separated into acidic fractions containing gangliosides. The obtained acidic fractions were enzyme-immunostained on TLC plates by making use of monoclonal antibody PyK-2.

The samples were spotted in a width of 6 mm at 1 cm from the bottom end of TLC plates and were developed with a solvent of chloroform, methanol and 2.5N aqueous ammonia in the volumetric ratio of 55:45:10. Out of the two plates treated in the same manner, one plate was then treated with an orcinol reagent to develop color, and the other plate was reacted with PyK-2 and then with peroxidase-labelled goat antimouse immunoglobulin antibodies. Bluish purple spots were detected by using 4-chloro-1-naphthol as a substrate.

Figure 9:
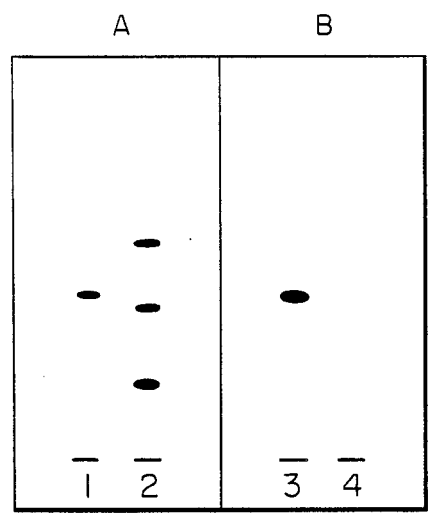
FIG. 9 are the spottings of the reactivity of N-glycolyl $GM_2$ ganglioside and the membrane fraction of rabbit thymus tissue, which were developed on the plates with the antibody PyK-2 by the enzyme immunostaining.

FIG. 9 shows the results thereof.

A shows the plate colored with an orcinol reagent and B shows the plate enzyme-immunostained. Nos. 1 and 3 were spotted with N-glycolyl $GM_2$ ganglioside in the amounts of 2 nmol and 3c pmol, respectively, and were then developed. Nos. 2 and 4 were spotted with 2nmol of sialic acid-containing acidic fractions extracted from the rabbit thymic tissues with the chloroform:methanol solution and were then developed.

It was confirmed in this example that rabbit thymic tissues, which was used as an immunogen in Example 1, has not any N-glycolyl $GM_2$ ganglioside. It was also confirmed that the hybridomas, which is capable of producing antibodies having a reactivity to N-glycolyl $GM_2$ ganglioside produced in Example I, were produced without giving any injection of N-glycolyl $GM_2$ ganglioside into NZB mouse.

What is claimed is:

1. A monoclonal antibody capable of specifically binding to a sugar chain containing NeuGc$\alpha$2-3 Gal- and not capable of binding to a sugar chain containing NeuAc.

2. The antibody of claim 1, wherein said sugar chain containing NeuGc$\alpha$2-3 Gal- has a Hanganatziu-Deicher antigen activity.

3. The antibody of claim 1, wherein said sugar chain containing NeuGc$\alpha$2-3 Gal- is a component of a glycolipid.

4. A monoclonal antibody capable of specifically binding to a sugar chain containing NeuGc$\alpha$2-3 Gal- and not capable of binding to a sugar chain containing NeuAc and a sugar chain containing $IV^3$ NeuGcn-LcOse$_4$ Cer.

5. The antibody of claim 4, wherein said sugar chain containing NeuGc$\alpha$2-3 Gal- has a Hanganatziu-Deicher antigen activity.

6. The antibody of claim 4, wherein said sugar chain containing NeuGc$\alpha$2-3 Gal- is a component of a glycolipid.

7. The monoclonal antibody of claim 4, wherein said antibody is not capable of binding to a sugar chain containing $VI^3$ NeuGc-nLcOse$_6$ Cer and a sugar chain containing N-glycolyl $GM_3$ ganglioside.

8. The monoclonal antibody of claim 7, wherein said antibody is YHD-04 or YHD-07.

9. A monoclonal antibody capable of specifically binding to a sugar chain containing NeuGc$\alpha$2-3 Gal- and not capable of binding to a sugar chain containing NeuAc and a sugar chain containing $VI^3$ NeuGc-nLcOse$_6$ Cer.

10. The antibody of claim 9, wherein said sugar chain containing NeuGc$\alpha$2-3 Gal- has a Hanganatziu-Deicher antigen activity.

11. The antibody of claim 9, wherein said sugar chain containing NeuGc$\alpha$2-3 Gal- is a component of a glycolipid.

12. A method for manufacturing a hybridoma which produces a monoclonal antibody having an ability to bind at least to N-glycolyl $GM_2$ ganglioside, in which said hybridoma is manufactured by cell fusion with myeloma cells and plasma cells of a mouse with autoimmune disease, and said mouse is not immunized with N-glycolyl $GM_2$ ganglioside, a sugar chain containing N-glycolyl $GM_2$ ganglioside or immunogens containing them.

13. A hybridoma which produces a monoclonal antibody capable of specifically binding to a sugar chain containing NeuGcα2-3 Gal- and not capable of binding to a sugar chain containing NeuAc.

14. The hybridoma of claim 13, wherein said sugar chain containing NeuGcα2-3 Gal- has a Hanganatziu-Deicher antigen activity.

15. The hybridoma of claim 13, wherein said sugar chain containing NeuGcα2-3 Gal- is a component of a glycolipid.

16. A hybridoma which produces a monoclonal antibody capable of specifically binding to a sugar chain containing NeuGcα2-3 Gal- and not capable of binding to a sugar chain containing NeuAc and a sugar chain containing $IV^3$ NeuGc-nLcOse$_4$ Cer.

17. The hybridoma of claim 16, wherein said sugar chain containing NeuGcα2-3 Gal- has a Hanganatziu-Deicher antigen activity.

18. The hybridoma of claim 16, wherein said sugar chain containing NeuGcα2-3 Gal- is a component of a glycolipid.

19. The hybridoma of claim 16, wherein said antibody is not capable of binding to a sugar chain containing $VI^3$ NeuGc-nLcOse$_6$ Cer and a sugar chain containing N-glycolyl $GM_3$ ganglioside.

20. The hybridoma of claim 19, wherein said antibody is YHD-04 or YHD-07.

21. A hybridoma which produces a monoclonal antibody capable of specifically binding to a sugar chain containing NeuGcα2-3 Gal- and not capable of binding to a sugar chain containing NeuAc and a sugar chain containing $VI^3$ NeuGc-nLcOse$_6$ Cer.

22. The hybridoma of claim 21, wherein said sugar chain containing NeuGcα2-3 Gal- has a Hanganatziu-Deicher antigen activity.

23. The hybridoma of claim 21, wherein said sugar chain containing NeuGcα2-3 Gal- is a component of a glycolipid.

24. The monoclonal antibody of claim 4, wherein said antibody is Pyk-2, YHD-04 or YHD-07.

25. The monoclonal antibody of claim 1, wherein said antibody has an ability to bind to N-glycolyl $GM_2$ ganglioside, N-glycolyl $GM_3$ ganglioside, $IV^3$NeuGc-nLcOse$_4$Cer and $VI^3$NeuGc-nLcOse$_6$Cer.

26. The monoclonal antibody of claim 1, wherein said antibody is YHD-02 or YHD-05.

27. The monoclonal antibody of claim 9, wherein said antibody is YHD-03.

28. The method of claim 12, wherein said myeloma cell is derived from a mouse.

29. The hybridoma PYK-2, ECACC Accession No. 86122001.

30. The hybridoma YHD-02, ECACC Accession No. 86122002.

31. The hybridoma YHD-03, ECACC Accession No. 87042208.

32. The hybridoma YHD-04, ECACC Accession No. 86122003.

33. The hybridoma YHD-05, ECACC Accession No. 86122004.

34. The hybridoma YHD-07, ECACC Accession No. 86122005.

35. The hybridoma YHD-06, FERM Accession No. BP-1839.

36. The hybridoma of claim 16, wherein said antibody is Pyk-2, YHD-04 or YHD-07.

37. The hybridoma of claim 13, wherein said antibody has an ability to bind to N-glycolyl $GM_3$ ganglioside, $IV^3$ NeuGC-nLcOse$_4$ Cer and $VI^3$NeuGc-nLcose$_6$Cer.

38. The hybridoma of claim 13, wherein said antibody is YHD-02 or YHD-05.

39. The hybridoma of claim 21, wherein said antibody is YHD-03.

* * * * *